United States Patent [19]

DuRoss

[11] 4,252,794
[45] Feb. 24, 1981

[54] GAMMA-SORBITOL POLYMORPH

[75] Inventor: James W. DuRoss, Smyrna, Del.

[73] Assignee: ICI Americas Inc., Wilmington, Del.

[21] Appl. No.: 105,543

[22] Filed: Dec. 20, 1979

[51] Int. Cl.³ .................... C07C 31/26; A21G 3/00; A61K 31/00; A61K 47/00
[52] U.S. Cl. .................................. 424/176; 568/852; 424/235; 424/361; 426/3; 426/660
[58] Field of Search .................... 568/852; 426/3, 660; 424/176, 235, 361

[56] References Cited

U.S. PATENT DOCUMENTS

| | | | |
|---|---|---|---|
| 2,755,220 | 7/1956 | Alford et al. | 568/852 |
| 3,039,927 | 6/1962 | Lafon | 424/235 |
| 3,445,528 | 5/1969 | Hales | 568/852 |
| 3,973,041 | 8/1976 | DuRoss | 426/3 |

FOREIGN PATENT DOCUMENTS 2409107  9/1974  Fed. Rep. of Germany .......... 426/660
2727778  1/1978  Fed. Rep. of Germany .......... 424/176

Primary Examiner—Joseph E. Evans

[57] ABSTRACT

A modified gamma-sorbitol polymorph having improved compressibility and hardness characteristics when formulated into a tablet while also exhibiting an absence or low degree of grit. Under a scanning electron microscope, the sorbitol polymorph of the invention is found to have a disrupted crystalline structure, substantial amounts of relatively large crystals not being coplanar with each other.

10 Claims, 4 Drawing Figures

GAMMA-SORBITOL POLYMORPH

BACKGROUND OF THE INVENTION

The present invention relates to sorbitol and its use in confectionary compositions.

Sorbitol has been utilized as a plasticizer and bodying agent in many products, a principal use presently being as a sweetner or excipient in confections or pharmaceutical tablets as set forth in U.S. Pat. No. 3,200,039. However, the hygroscopic nature of sorbitol may limit the conditions under which a tablet press, used to prepare lozenges or tablets, can be operated without jamming. Further, problems may exist with respect to preparing a sorbitol product which has sufficient crystallinity to be tableted.

Amorphous uncrystallized sorbitol, or "glass" is characterized by an absence of a significant heat of fusion. The large percentage of "glass," e.g. about 40%, in many commercially available sorbitol products results in a material which has a tendency to soften when tableted, necessitating high pressures to obtain satisfactory lozenge hardness, if such can be obtained at all.

In order to prepare sorbitol with a high crystallinity, methods including the cooling of a hot solution or melt with added sorbitol crystals have been disclosed in U.S. Pat. Nos. 2,483,254; 2,594,863; 3,308,171 and 3,330,874, German Auslegeschrift No. 1,115,726, Japanese Patent Application No. 1970-119151 and Patentschrift No. 83,341 of the German Democratic Republic. Other crystallization or solidification techniques are described in U.S. Pat. Nos. 2,315,699 and 2,566,410 as well as in German Patentschrift No. 76,487.

A procedure for preparing a substantially crystalline sorbitol is disclosed in my U.S. Pat. No. 3,973,041. The sorbitol produced comprises at least about 80% of the gamma sorbitol polymorph and the method involves a simultaneous mixing and cooling of a sorbitol magma in a continuous mixer such as that described in U.S. Pat. No. 3,618,902. Other mixing or kneading apparatuses are set forth in U.S. Pat. Nos. 3,195,868; 3,198,491; 3,318,606; 3,419,250; 3,423,074; 3,490,750; 3,873,070 and 3,900,187. The compounding of various food compositions is reported in U.S. Pat. Nos. 2,847,311; 3,694,227 and 3,806,617.

Highly crystalline sorbitol, such as that described in U.S. Pat. No. 3,973,041 may not meet tablet manufacturers needs since some of the more crystalline sorbitol tends to have a limited degree of crystal copenetration under pressure during tableting. Added pressure may cause "capping", the separation of tablet into two separate pieces. This problem is particularly encountered when the formulator uses a weight-to-weight substitution of a highly crystalline sorbitol with a dense crystal matrix for a conventional sorbitol preparation, for example, sorbitol with a low degree of crystallinity. Further, when the dense crystalline sorbitol is used as a weight-to-weight substitution in chewing gum formulations, it may be found that the gum is too soft to process in an efficient manner and an increased amount of crystalline sorbitol with a corresponding decrease in the volume of plasticizer is required to achieve the desired consistency.

It is therefore an object of the invention to provide a gamma sorbitol product, at least about 80% crystalline, which possesses excellent tableting characteristics and which will also increase the shelf life of sorbitol-containing chewing gums produced therewith, while at the same time allowing the formulator to make a substantially weight-to-weight substitution for the conventional crystalline sorbitol which is about 60% to 90% crystalline and which contains one or more crystalline polymorphs.

As used in the present specification, "sorbitol" is inclusive of the compound sorbitol with or without minor amounts of mannitol, either material being commercially accepted in the confectionary art as sorbitol. Additionally, the sieve cut specifications given in the specification, e.g. "−20/+60 mesh cut," refer to stainless steel sieves of the U.S. Standard Screens.

DETAILED DESCRIPTION OF THE INVENTION

Figure 1A:
FIGS. 1a and 1b depict typical scanning electron photomicrographs of the sorbitol product produced according to Reference Example I, the figures being at 100X and 2000X magnification, respectively.

The modified gamma-sorbitol of the invention is shown under a scanning electron microscope at a magnification of 2000X to have a loosely packed structure, the crystals having a width or diameter size of at least about 1.0 micron and preferably up to about 3 microns, e.g. about 1.0 to 1.5 microns, which crystals are randomly or substantially randomly oriented. The disrupted crystalline material of the invention, for a −20/+60 mesh cut has a surface area of at least about 1.0 square meters per gram ($m^2/g$) dry basis (d.b.), preferably at least about 1.1 $m^2/g$ and preferably less than 2.5 $m^2/g$.

In contrast, conventional gamma-sorbitol at 2000X may be shown, under a scanning electron microscope, to have a tightly packed crystalline matrix with the crystals being oriented in the same direction, e.g. perpendicular to the extruder plate of the mixer-crystallizer used in the production of sorbitol in the shape of dowel sticks. The crystals of such commercially available dense gamma-sorbitol have a diameter or width on the order of up to about 0.3 to 1.0 microns and the surface area of the product, for a −20/+60 mesh cut, is lower than about 0.7 $m^2/g$ d.b.

Amorphous material presents significant handling problems in that it readily absorbs water vapor and when left at ambient conditions will rapidly go into solution due to its hygroscopicity. The modified gamma-sorbitol of the invention will resist water absorption and may thus be compounded into various preparations which will be stable to humidity for extended periods.

The randomly oriented nature of the modified gamma-sorbitol of the invention has been found to significantly affect its compacting properties during tableting. Thus, while the virtual absence of interstitual spacing in conventional gamma-sorbitol results in a lack of copenetration during tableting, the loosely-packed invention material will compact more readily during tableting and the copenetration of the crystals will allow a lowering of the tableting pressures needed in the production of a standard size and weight tablet. This results in a significant savings in energy and apparatus wear. Further, lower tableting pressures also serve to reduce the risk of "capping." The compression value and thus the measure of copenetration during tableting of the sorbitol polymorph of the invention may be determined by preparation of a standard tablet and measurement of its thickness. Preferably, the tablet is ⅜ inch in diameter, round and flat (a short cylinder) with bevelled edges, weighs 1.00±0.05 grams and consists of a charge of 99.5% by weight of a −20/+60 mesh powder of the polymorph and 0.5% by weight of magnesium stearate. Such a tablet may be formed in a Stokes B-2 Press at about 3.2 tons pressure on the two flat surfaces of the tablet. The compression value of sorbitol according to the invention is about 3.82 millimeters (mm) or below, preferably about 3.80 mm or below, for such a ⅜ inch diameter tablet.

The higher copenetration achievable by the crystals of the modified gamma-sorbitol of the invention results in a Strong Cobb Arner hardness value of at least about 22 kilograms (Kg), preferably at least about 24 or 26 Kg, for a tablet produced as described by the tableting procedure in the preceeding paragraph and in Reference Example I.

The modified crystalline gamma-sorbitol of the invention is characterized additionally by a crystalline content of at least about 80% by weight, preferably at least about 90% and most preferably about 100%, with the remainder being, for example, the amorphous "glass" sorbitol. Further, the sorbitol polymorph of the invention has a melting point of about 100° to 101° C.

Preferably, the modified gamma-sorbitol of the invention is produced by a process, hereinafter described, which utilizes a molten sorbitol feed without the addition of seed sorbitol to promote crystallization.

It has been found that the product of the invention has significantly reduced "grit." The "grit," or "sandy" quality of a sorbitol-based tablet reduces commercial acceptance of the product since it may be considered an unpleasant quality of the tablet when dissolving in the mouth. The "grit" in a sorbitol tablet is evidenced by a rough texture as other portions of the tablet dissolve faster than the particles which have a more dense crystalline matrix.

The modified gamma-sorbitol of the invention may be prepared by the process described in U.S. Ser. No. 463,048 filed Apr. 19, 1974, now abandoned, in the name of Kasehagan with, however, certain modifications as set forth below.

The sorbitol polymorph of the invention is preferably made by a process wherein molten sorbitol at a temperature of about 96°-97° C. is fed to heavy duty paste or viscous material mixer rather than a process wherein seed and molten materials are combined, as in the Dravo pelletizer process. In a water-cooled mixer, the molten magma is simultaneously cooled and kneaded. The preferred type of mixer is a continuous twin shaft mixer of the intermeshing type. Mixers of this type are discussed in "Chemical Engineer's Handbook", Fifth Edition edited by R. H. Perry and C. H. Chilton (1973) pages 19-21. Characteristics of these mixers are that they include intermeshing kneader blades mounted on two parallel shafts which rotate in the same direction at the same speed, with close blade-to-wall and blade-to-blade clearances.

A preferred continuous mixer is the high shear Readco Continuous Processor, made by Teledyne Readco of York, Pa. The mixer in the experimental work described herein is such a device and is the mixer shown and described in U.S. Pat. No. 3,618,902 except that the side discharge opening shown in the patent was replaced with an extruder section which included twin conveyor screws, a die plate, and an extrusion nozzle. The mixers shown in either U.S. Pat. No. 3,419,250 or in U.S. Pat. No. 3,618,902 (both assigned to Teledyne Inc.) can be used without modification; however, the plastic magma which is formed in the present process is much more easily handled if the mixer is equipped with an extrusion nozzle or plate. Other high shear continuous twin screw mixers which impart a high shearing force at low shaft speed to the material being processed can also be used. Such mixers include the Baker Perkins Multi-Purpose (M-P) Mixer, made by Baker Perkins, Inc. of Sagnaw, Mich., and the ZSK Twin Screw Compounding Extruder made by Werner and Pfleiderer Corporation of Stuttgart, Germany. The Baker Perkins mixer is shown in U.S. Pat. Nos. 3,195,868 and 3,198,491. Alternative blade configurations which can be used in mixers of this type are shown in U.S. Pat. Nos. 3,423,074 (assigned to Baker Perkins) and 3,490,750 (assigned to Teledyne, Inc.). These mixers are available in various diameters and horsepower ratings, depending on the throughput required.

Preferably, a Readco Continuous Processor, with kneader blade diameters of 5, 15 or 24 inches and feed and/or discharge screws, may be utilized. Further, the discharge nozzles are preferably provided with heating elements in order to melt the surface of the partially solidified cylindrical ribbon of exiting sorbitol to insure a smooth discharge. Thus, a process for producing the improved gamma-sorbitol polymorph of the invention involves, in general, continuously introducing a feed comprising molten sorbitol into an elongated mixing zone having shaft means and a plurality of kneader blades mounted on the shaft means, the configuration of the kneader blades being such as to provide restricted clearances between the blades and the adjacent walls; simultaneously cooling and kneading the molten sorbitol as it passes through the mixing zone until a plastic magma of molten sorbitol and a substantial portion of gamma-sorbitol crystals is obtained; and continuously discharging the plastic magma from the mixing zone through an extrusion orifice and further cooling the plastic magma to ambient temperature forming the modified gamma-sorbitol polymorph.

Confectionary compositions according to the invention may be prepared by compounding the gamma sorbitol polymorph of the invention with flavoring agents and/or other additives, such as adjuncts, artificial sweeteners and coloring, as known in the art. In particular, citric acid is an excellent flavor enchancer for use with the polymorph of the invention. Another confectionary using the gamma sorbitol polymorph of the invention is a chocolate composition, such as a bar, which may be made by a conventional process with cocoa, chocolate liquor, milk powder, vanillin, an emulsifier and the sorbitol polymorph of the invention.

Pharmaceutical compositions such as tablets may be made using the gamma sorbitol polymorph of the invention as an excipient in combination with a medicinal agent such as vitamin C, aspirin or an antacid. Tablets of the compositions may be prepared as described in Reference Example I with the proper additive.

REFERENCE EXAMPLE I

Sorbitol containing 0.2 to 0.4% by weight water and obtained from ICI Americas Inc. of Wilmington, Del., 19897, was melted at about 100° C. and continuously fed to a 5 inch Readco continuous mixer similar to that described in U.S. Pat. No. 3,618,902. The mixer had a length of 36 inches, a nominal diameter of 5 inches, dual mixer blade shafts, a heat exchanger surface area of about 6 square feet, an internal volume exclusive of space occupied by shafts, kneader blades and conveyor screws of 3.75 gallons and a nominal power of about 10 horsepower. The operating conditions of the run included a shaft rotation speed of 35 rpm, a blade tip speed of 45.8 feet per minute and an air flow through the mixer of 0.31 cubic feet per minute as sparged through a sintered metal tube inserted in the feed line. The sparged air was preheated to about 110° C. to prevent premature crystallization and the mixer was otherwise closed to the atmosphere.

Solid sorbitol production through the mixer, maintained as described in the preceeding paragraph, was stabilized with a production rate of 275 pounds per hour and a water jacket temperature of about 15° C.

After the cylindrical ribbon of sorbitol discharged from the mixer had cooled, a sample was ground in a Waring blender and a $-20/+60$ mesh cut was obtained. A surface area measurement and scanning electron micrograph were taken of the sieved powder as explained below.

The surface area measurement was conducted by the $N_2$ Displacement Test as generally described in the article "BET Surface Area by Nitrogen Absorption" by S. Brunauer, et al in the Journal of the American Chemical Society, 60, p. 309 (1938). In general, when values below about 0.6 $m^2/g$ are obtained the figures are not considered as accurate as those above this value. For the sample obtained in this Example, a measurement of about 0.7 $m^2/g$ was found.

Figure 1B:

Scanning electron micrographs were taken of the powder and these are shown in FIGS. 1a and 1b. FIG. 1a was taken at a magnification of 100X and is a micrograph of the longitudinal area of a granule of the sorbitol powder. FIG. 1b is a longitudinal area micrograph at a magnification of 2000X. As with all other micrographs described in this specification, the images depicted in FIGS. 1a and 1b were selected by the operator of the micrograph apparatus as typical of a substantial number of images observed for the particular sample. The micrographs were made by Micron, Inc. of Wilmington, Del., 19807 with a Scanning Electron Microscope Model 700S from Materials Analysis Company operating at 20,000 volts.

FIG. 1a indicates that the sample powder has a hard and dense texture which is confirmed by the relatively low surface area measurement of about 0.7 $m^2/g$, surface area being inversely related to density. The angular and jagged surfaces of the particles in FIG. 1a are predictive of a gritty product which is undesirable in many tableting applications. In fact, a $-20/+60$ mesh powder of the product of this example was found in blind taste tests to be substantially more "gritty" than the products of the invention obtained as described in Examples I and II.

FIG. 1b, a longitudinal view at 2000X, indicates a closely packed and regular crystal structure which one would expect not to compact well on tableting. The high degree of coplanarity of relatively thin acicular microcrystals, i.e. on the order of 0.5 up to 1.0 micron, is indicative of a material which has little "give" on being tableted. Such a non-giving material produces a tablet which is more easily disintegrated and which is not as hard as tablets produced from more easily compacted powders, even though individual crystals as viewed at 100X are more gritty. In fact standard weight tablet thickness tests and hardness measurements of the tablets, as detailed below, confirm predictions made on the basis of the micrographs.

A tablet thickness (compressibility) test was conducted on the product of this Reference Example by mixing a 300 gram granulation containing 99.5% by weight of the $-20/+60$ mesh cut of sorbitol and 0.5% of magnesium stearate. The granulation was inserted into the feed hopper on a Stokes B-2 Press fitted with a ⅝ inch diameter flat-faced, beveled edge punch obtained from Stokes Compacting Equipment of Hightstown, N.J. The press was set up to produce a 1.00±0.05 gram tablet and at a compression pressure of 3.2 tons, the resulting tablet had a thickness of 3.86 mm.

A hardness test was then conducted on the ⅝ inch diameter tablet described in the preceeding paragraph. The hardness testing apparatus was a Model B-255 Strong Cobb Arner Hardness Tester made by Strong Cobb Arner, Inc. of Cleveland, Ohio and described in U.S. Pat. No. 2,645,936 issued July 21, 1953 to A. Albrecht. In the test, the ⅝ inch tablet disintegrated when a force of 17 kg was applied by the apparatus.

The gamma crystal content of a $-20/+60$ mesh cut of the product of this Example was determined by Differential Scanning Calorimetry (DSC) to be 91.9% by weight.

A melting point of 99° C. was found for a $-20/+60$ mesh cut of the product of this Example.

EXAMPLE I

Molten sorbitol was fed to the 5 inch Readco Mixer described in Reference Example I. The apparatus operating conditions were a shaft rotation speed of 37 rpm, a blade tip speed of 48.5 feet per minute, a production rate of sorbitol of 411 pounds per hour and a water jacket temperature of about 15° C. with the feed hopper being closed to the atmosphere.

A surface area measurement was conducted on a $-20/+60$ mesh cut of the solid product according to the invention by the procedures of Reference Example I. A surface area of 1.55 $m^2/g$ was found for the sorbitol of this Example.

Figure 2A:
FIGS. 2a and 2b depict typical scanning electron photomicrographs of the sorbitol product of the invention produced according to Example I, the figures being at 100X and 2000X magnification, respectively.
Figure 2B:

Scanning electron micrographs of a $-20/+60$ mesh cut of the sorbitol of the present invention from this run are shown in FIGS. 2a and 2b. FIG. 2a at 100X magnification is a longitudinal view of a granule and it can be seen that it is a rounded formation which is substantially less jagged than the comparable FIG. 1a at the same magnification. As in Reference Example I, the appearance of the material in a micrograph at 100X power was predictive of grit taste tests. A $-20/+60$ mesh cut of the product of this Example according to the invention was found by a taste test panel to have no grit.

FIG. 2b at 2000X power shows microcrystals substantially wider and flatter but shorter than those in FIG. 1b. Measurements of the crystals of FIG. 2b indicate a width of about 1.0 to 1.5 microns. Additionally, the FIG. 2b microcrystals are more randomly oriented and the greater amount of open space between groupings of microcrystals suggests a material which is more compressible, i.e. which has more "give", during tableting. As shown below, the sorbitol of Example I in tablet thickness tests and hardness measurements did, in fact, behave as one would predict from the micrograph evidence. The tablet was harder, i.e. more resistant to disintegration under pressure, and thinner than the tablet produced in Reference Example I.

A tablet thickness (compressibility) test was conducted on the product of Example I in accordance with the material amounts and procedures set forth in Reference Example I. The tablet produced was found to have a thickness of 3.76 mm, indicative of a more compressible sorbitol than that from Reference Example I.

A hardness test on the 3.76 mm tablet described in the above paragraph was then conducted by the procedure mentioned in Reference Example I. The tablet of sorbitol according to the invention disintegrated when a force of 24 Kg was applied with the Strong Cobb Arner Hardness Tester.

The gamma crystal content of a −20/+60 mesh cut of the product of this Example was found by DSC to be 100% by weight.

The melting point of a −20/+60 mesh cut of the product of the Example according to the invention was 100° C.

EXAMPLE II

Molten sorbitol was fed through a closed hopper to the 5 inch Readco mixer described in Reference Example I. The Readco mixer was operated at a shaft speed of 37 rpm, a blade tip speed of 48.5 feet per minute, a production rate of 33 pounds per hour and a water jacket temperature of about 15° C., the water jacket being maintained at only 23% capacity. It is believed that the lower volume of coolant results in a greater amount of sorbitol exiting the apparatus in an unsolidified state, thus involving a greater amount of crystallization outside of the mixer.

A surface area measurement was conducted on a −20/+60 mesh cut of this product according to the invention in accordance with procedures of Reference Example I. A surface area of 1.74 m²/g was thus found for the sorbitol polymorph of this example.

A sample of the −20/+60 mesh cut was tableted for a tablet thickness (compressibility) test on a Stokes B-2 Press as in Reference Example I. The tablet was found to have a thickness of 3.78 mm, which value is comparable to that of Example I and indicative of a more compressible sorbitol polymorph than that produced in Reference Example I.

A hardness test on the 3.78 mm tablet was then conducted by the hardness testing procedure in Reference Example I. The tablet disintegrated at a pressure of 23 Kg indicating an integral and hard tablet.

In a taste test of the product of Example II, pannelists generally found only a very slight amount of grittiness.

As in Example I, a −20/+60 mesh cut of the product of this Example according to the invention had a gamma crystal content, as determined by DSC, of 100% and a melting point of 100° C.

EXAMPLE III

Peppermint flavored confectionary tablets may be formulated with a gamma sorbitol polymorph according to the present invention.

Sorbitol according to the invention was prepared in a 24 inch diameter Readco Continuous Processor which is similar to the 5" Readco Continuous Processor described previously. Flavor was provided by the addition to the base tablet formulation of peppermint oil absorbed on a silica gel. Tablets were prepared by mixing the following ingredients:

|  | Weight (in grams) | % by weight |
|---|---|---|
| 1. Gamma sorbitol polymorph of the invention (−20/+60 mesh cut) | 480 | 96% |
| 2. Magnesium stearate | 5 | 1% |
| 3. Peppermint oil (from American Chicle Co.) | 5 | 1% |
| Silica gel (Syloid 244 from W. R. Grace & Co.) | 10 | 2% |
|  | 500 | 100% |

After mixing the ingredients in a Patterson-Kelly V-Blendor, a 1.00±0.05 gram charge was tableted from the formulation as described in Reference Example I. The ⅝ diameter tablet was found to have a compressibility value of 3.78 mm and a hardness of 23 kg., both values being basically determined as described in Reference Example I.

EXAMPLE IV

Chewing gum may be prepared by the procedure of Example I of my U.S. Pat. No. 3,973,041, substituting the gamma sorbitol powder in the Example of the patent with the gamma sorbitol polymorph of the invention having the following particle size specifications:

| |
|---|
| 0.5% maximum retained on a 30 mesh screen, |
| 5% maximum retained on a 40 mesh screen, |
| 45% minimum through a 80 mesh screen, |
| 12% maximum through a 200 mesh screen. |

What is claimed is:

1. A modified gamma-sorbitol polymorph having improved tableting properties characterized in that the modified gamma-sorbitol has:
   (a) a disrupted and loose crystal structure visible on a scanning electrom microscope at 2000X power;
   (b) a surface area value for a −20/+60 mesh powder of the polymorph of at least about 1.0 square meter per gram;
   (c) a compression value of about 3.82 mm or less, said compression value being the thickness in millimeters of a round, flat, beveled edge tablet which is ⅝ inch in diameter and which is formed under 3.2 tons pressure on a 1.00±0.05 gram charge consisting of 99.5% by weight of a −20/+60 mesh powder of the polymorph and 0.5% by weight of magnesium stearate;
   (d) a Strong Cobb Arner hardness value of at least about 22 kilograms for the round tablet of paragraph (c);
   (e) a gamma-sorbitol crystal content of at least about 80% by weight; and
   (f) a melting point of about 100° to 101° C.

2. The modified gamma-sorbitol polymorph of claim 1, wherein said polymorph is further characterized by crystals widths of at least about 1.0 micron as visible on a scanning electron micrograph at 2000X magnification.

3. The modified gamma-sorbitol polymorph of claim 1, wherein said surface area is at least about 1.1 square meters per gram.

4. The modified gamma-sorbitol polymorph of claim 1, wherein said crystal content is at least about 90% by weight.

5. The modified gamma-sorbitol polymorph of claim 4, wherein said crystal content is about 100% by weight.

6. The modified gamma-sorbitol polymorph of claim 1, wherein said Strong Cobb Arner hardness value is at least about 24 kilograms.

7. A confectionary composition comprising the modified gamma-sorbitol polymorph of claim 1 and a flavoring agent.

8. The composition of claim 7, wherein said confectionary composition is a tablet.

9. The composition of claim 7, wherein said confectionary composition is a chewing gum.

10. A pharmaceutical composition comprising the modified gamma-sorbitol polymorph of claim 1 and a pharmaceutical agent.

* * * * *